(12) United States Patent
Sedlmair et al.

(10) Patent No.: US 10,588,588 B2
(45) Date of Patent: Mar. 17, 2020

(54) METHOD FOR THE FULLY AUTOMATIC DETECTION AND ASSESSMENT OF DAMAGED VERTEBRAE

(71) Applicant: Siemens Aktiengesellschaft, München (DE)

(72) Inventors: Martin Sedlmair, Zirndorf (DE); Michael Sühling, Erlangen (DE); Alexey Tsymbal, Erlangen (DE); Dimitrij Zharkov, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 807 days.

(21) Appl. No.: 14/887,724

(22) Filed: Oct. 20, 2015

(65) Prior Publication Data
US 2016/0113612 A1   Apr. 28, 2016

(30) Foreign Application Priority Data
Oct. 28, 2014   (DE) .................. 10 2014 221 942

(51) Int. Cl.
*A61B 6/00*   (2006.01)
*A61B 6/03*   (2006.01)

(52) U.S. Cl.
CPC .............. *A61B 6/505* (2013.01); *A61B 6/032* (2013.01); *A61B 6/5217* (2013.01); *A61B 6/482* (2013.01); *A61B 6/583* (2013.01)

(58) Field of Classification Search
CPC ............................. A61B 6/505; A61B 6/5217
See application file for complete search history.

(56) References Cited

U.S. PATENT DOCUMENTS

| | | | |
|---|---|---|---|
| 2003/0176780 A1* | 9/2003 | Arnold | G06T 7/0012 600/407 |
| 2004/0120922 A1 | 6/2004 | Burke | |
| 2008/0279435 A1* | 11/2008 | Arnold | G06T 7/0012 382/131 |
| 2012/0143090 A1 | 6/2012 | Hay et al. | |
| 2012/0183193 A1 | 7/2012 | Wels et al. | |
| 2014/0219548 A1 | 8/2014 | Wels et al. | |

FOREIGN PATENT DOCUMENTS

EP   2562690 A2   2/2013

OTHER PUBLICATIONS

Y. Zheng, "Fast Automatic Heart Chamber Segmentation From 3D CT Data Using Marginal Space Learning And Steerable Features"; Oct. 21, 2007, IEEE 11th International Conference on Computer Vision, 8 pages.

(Continued)

*Primary Examiner* — Hien N Nguyen
(74) *Attorney, Agent, or Firm* — Harness, Dickey & Pierce, P.L.C.

(57) ABSTRACT

A method is disclosed for the automatic determination of the bone density and a method is disclosed for the automatic detection and characterization of spinal column fractures. Both methods enable the fully automatic detection and assessment of damaged vertebrae and reliably enable an analysis of the state of the vertebrae with a high accuracy rate. A computed tomography system to carry out either of the methods is further disclosed.

11 Claims, 4 Drawing Sheets

(56) References Cited

OTHER PUBLICATIONS

A. Tsymbal, "Learning Discriminative Distance Functions for Case Retrieval and Decision Support"; Transactions on Case-Based Reasoning, vol. 3, No. 1, 16 pages; ISSN: 1867-366X; ISBN: 978-3-94-050117-2; XP055090974; 2010.

Genant et al., "Vertebral Fracture Assessment Using a Semiquantitative Technique," Journal of Bone and Mineral Research, Nov. 9, 1993, p. 1137-1148, vol. 8, Mary Ann Liebert, Inc., Publishers.

* cited by examiner

METHOD FOR THE FULLY AUTOMATIC DETECTION AND ASSESSMENT OF DAMAGED VERTEBRAE

PRIORITY STATEMENT

The present application hereby claims priority under 35 U.S.C. § 119 to German patent application number DE 102014221942.6 filed Oct. 28, 2014, the entire contents of which are hereby incorporated herein by reference.

FIELD

At least one embodiment of the invention generally relates to a method for the automatic determination of the bone density and a method for the automatic detection and characterization of spinal column fractures.

BACKGROUND

Osteoporosis and bone tumors are two of the most frequent diseases of the spine, in particular of the vertebral bodies. A symptom of the diseases is inter alia a decreasing bone strength, which results in a premature degeneration of the vertebral bodies and thus results in a high risk of bone fractures for the patients.

Thanks to modern medicine there are, at least in the industrialized countries, an ever increasing number of old people. The number of cases in which vertebral fractures are discovered in patients is rising rapidly on account of this development. For example, osteoporosis is one of the most frequently encountered diseases in Japan and it is estimated that 12 million people are affected there. Since the average age of the population is currently increasing in all the industrialized nations, the number of disease cases is expected to rise even further in future.

Early detection of osteoporosis or of bone tumors is of great importance since with early treatment the risk of bone fractures can be significantly reduced and the quality of life of the persons affected can be decisively enhanced thereby. Although damage which has already occurred is often irreversible, an early medication-based treatment for example in the case of osteoporosis can prevent further bone fractures. Osteoporosis is by far the most frequent cause of fractures of the vertebral bodies.

Early detection of fractures or cracks in the vertebral bodies is however difficult because the causative illnesses often do not develop symptomatically. For this reason, changes in the bone tissue which could result in fractures are often only discovered when the spinal column is being examined radiologically for other reasons.

There is moreover as yet no consensus on when a change in the bone is to be regarded as a fracture and how this is to be diagnosed.

Various methods and radiographic systems for the detection of vertebral fractures and for risk assessment have already been proposed in the past. Many vertebral fractures are however still not being diagnosed. Even if they are diagnosed, the diagnosis is often not passed on. And an existing diagnosis is not taken into consideration in all cases with regard to the treatment of the patients.

Apart from using 2D X-ray absorption measurements (DXA), bone density measurements are normally carried out using 3D measurements of the bone mineral density (BMD) by means of quantitative CT (QCT) or dual-energy CT. To this end, a measurement region (region of interest, ROI) within the vertebral bodies is set manually by the user or semi-automatically. The CT data from the ROI is then evaluated in order to obtain data relevant to the density determination such as the average HU value or the bone mineral density. Either a calibration dummy or the dual-energy information can be used for the latter.

In order to determine the degree of compression of the vertebral bodies and the risk of a fracture, the height of the vertebral bodies is usually measured manually. Genant et al. (Genant, Wu, van Kuijk, Nevitt, Bone Miner Res, 1993, 8, 1137-48) have presented a semi-quantitative method by means of which the degree of degeneration of the vertebral bodies can be categorized from measuring the height of the vertebral bodies.

Fractures are accompanied by a change in shape of the vertebral bodies, in particular the loss of parallelism of the endplates, breaks or cracks in the external bone structure (cortical bone) and usually a reduced anterior, middle or posterior height. With the method, one speaks of a fracture when the loss in height exceeds 20% of the original height.

The degree of the height loss determines the associated grade of the vertebral fracture. Fractures are categorized as wedge fracture, biconcave fracture or compression fracture, depending on whether the height loss is greatest in the anterior, middle or posterior region of the vertebral body.

The method of Genant et al. is often considered to be the best method for the determination of vertebral fractures on account of the good reproducibility thereof. With this method, vertebral fractures can be well differentiated from other types of deformation. In particular, this method delivers useful information regarding the severity of the fractures and delivers prognoses for their further development.

Siemens AG presented a method for the segmentation of vertebral bodies in a publication in 2013.

US 2012/0183193 A1 shows a method which can be used to automatically detect vertebral fractures. The assessment of the fractures is however carried out manually with this method, which can be extremely time-consuming.

US 2014/0219548 A1 presents a machine learning algorithm which can evaluate 3D images with the aid of geometric structures (landmarks).

EP 2 562 690 A2 presents a method which can be used to compare a measured data set with a reference data set with the aid of random forest decision trees inter alia.

Even though a number of methods therefore exist for the detection of vertebral fractures, the detection of vertebral fractures and the risk assessment remain error-prone, in particular in the case of semi-automatic methods. The detection of very slight fractures is particularly difficult and is recognized only in approximately half of cases.

SUMMARY

At least one embodiment of the present invention is directed to a method for the fully automatic detection and assessment of damaged vertebrae, which reliably enable an analysis of the state of the vertebrae with a high accuracy rate.

A method of at least one embodiment comprises:
a) provision of at least one 3D CT scan of a person to be examined;
b) detection of at least one vertebral body in a CT image based on the 3D CT scan;
c) determination of the contour of the cortical bone of a vertebral body by means of a suitable algorithm on the basis of the development of the HU values; and d) reduction of the contour thus found by a configurable marginal area or a configurable marginal volume to an inner area or an inner volume.

Also belonging to an embodiment of the invention is a method for the automatic detection and characterization of spinal column fractures, which comprises:

a) provision of at least one 3D CT scan of a person to be examined;
b) detection of the spinal column in a CT image based on the 3D CT scan;
c') segmentation of the vertebral bodies in the CT image;
d') detection of fractures;
e') characterization of the fractures.

An embodiment of the invention relates to a computed tomography system which includes a central processing unit or a computer for the evaluation of image data, wherein the method according to an embodiment of the invention is implemented on the central processing unit or the computer of the computed tomography system. Such a computed tomography system proves to be very advantageous because it enables fracture analyses to be carried out fully automatically.

Ideally the method according to an embodiment of the invention is part of a computer program for use with a central processing unit or a computer for the evaluation of image data from a computed tomography system.

By preference, the computer program containing the method according to the invention is stored on a data medium.

Alternatively, the computer program can however also be stored in a network to which the computer in the computed tomography system has access.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

A method of at least one embodiment comprises:
a) provision of at least one 3D CT scan of a person to be examined;
b) detection of at least one vertebral body in a CT image based on the 3D CT scan;
c) determination of the contour of the cortical bone of a vertebral body by means of a suitable algorithm on the basis of the development of the HU values; and
d) reduction of the contour thus found by a configurable marginal area or a configurable marginal volume to an inner area or an inner volume.

Optionally, a determination of the averaged bone density value can take place thereafter with the aid of the HU values in the inner and/or outer area or the inner and/or outer volume.

The detection of the vertebral bodies in step b) can also comprise a segmentation of the vertebral bodies in the CT image.

The provision of at the least one CT scan in step a) can comprise making such a CT scan or an upload from a storage medium or from a data network.

Steps a) and b) are based on known methods which automatically detect the endplates of the vertebral bodies (syngo.via CT Bone Reading).

In at least one embodiment, a method is capable of detecting the relevant volume within the vertebral bodies. The lower and upper endplates of each vertebral body are used as input.

Each vertebral body can for example be divided into image slices which are arranged orthogonally with respect to the course of the spinal column. The algorithm would then commence with the middle slice and then work its way as far as the lower and upper endplates.

In a variant of the method, virtual beam paths which run from the middle of the image slice to the edges are constructed for each individual slice.

In this case the middle can be the actual middle of the vertebral body, the middle of the inner vertebral body (without spinous processes) or an imaginary middle region which is essentially situated in the middle of the vertebral body.

The beam paths can cover a 360° angle or also only an angular range if for example one wishes to exclude the spinous processes of the vertebral body from the ascertainment of the HU values.

The HU values along each beam produce a graph. The local maxima are determined with the aid of a low-pass filter. Only one of the maxima belongs to the contour of the cortical bone (corticalis).

In a continuation of the variant, in order to find this contour the maxima are used as nodes of a weighted (2D) graph. A "shortest path" algorithm is employed in order to find the optimum path between the maxima of all the beam paths. In this situation, the algorithm decides on the basis of the HU value of the maxima and the path distance lying between the maxima which local maximum is used in each case for the determination of the contour of the vertebral body.

In a variant of the method, a modified Dijkstra's algorithm is used for this purpose.

When the contour has been determined, the contour is narrowed toward the middle in order to exclude the cortical bone from the density measurement. The cortical bone is significantly harder than the inner part.

This procedure is repeated for all the slices of the vertebra. Alternatively, the determination could equally take place in a volume of interest which essentially corresponds to the sum of the image slices.

The CT data is evaluated within the volume thus ascertained.

In an advantageous variant of the method according to an embodiment of the invention, the bone density value ascertained is automatically compared with reference data which contains statements regarding the probability of an osteoporosis as a function of the bone density value.

By preference, in the variant of the method according to an embodiment of the invention patient data such as for example (but not limited to) age and known pre-existing conditions is taken into consideration for the comparison with the table. However, further data relating to the patient's case history can also be taken into consideration.

A further variant of the method according to an embodiment of the invention is characterized in that the bone density is determined by using dual-energy data.

Alternatively, the bone density can be determined by the use of a dummy measured in step a) together with the person to be examined.

A further alternative is to ascertain the bone density by using normalized or calibrated CT attenuation values which are ascertained on the basis of the accelerating voltage of an X-ray source used during the measurement. It is furthermore proposed to determine the CT attenuation values in the cortical bone, which has been previously identified, and to determine the relative attenuation of the trabeculae in comparison with the cortical bone. Relative attenuation coefficients determined in such a manner are less dependent on the parameters used.

Also belonging to an embodiment of the invention is a method for the automatic detection and characterization of spinal column fractures, which comprises:
a) provision of at least one 3D CT scan of a person to be examined;
b) detection of the spinal column in a CT image based on the 3D CT scan;
c') segmentation of the vertebral bodies in the CT image;
d') detection of fractures;
e') characterization of the fractures.

Optionally, an output of the results can take place divided into diagnostic categories, in particular risk of fracture, malignancy and/or disease type.

The provision of at least one CT scan in step a) can comprise making such a CT scan or uploading from a storage medium or from a data network.

The algorithm begins with the calculation of 3D bounding boxes around the vertebral bodies. The segmentation of the vertebral bodies in step c') can be based on geometric features (landmark-based), for example the corner points of the vertebral body or it can be based on the "marginal space learning" algorithm of Zheng et al. (Zheng, Barbu, Georgecu, Scheuring, Comaniciu, Int'l Conf. Computer Vision, 2007, the entire contents of which are hereby incorporated herein by reference).

This enables a complete segmentation of the vertebral bodies, which results in a 3D network that surrounds the vertebral bodies. In addition the trabecula (spongiosa) can, for example by means of the steps stated in claim 1, be differentiated from the cortical bone.

The detection of the vertebral fractures takes place thereafter. This can happen in three ways.

On the one hand, the detection in step d') can take place by way of an approach based on geometric features, wherein one can use the geometric features which have already been used for segmentation of the spinal column in the previous step. This procedure corresponds to the automation of the Genant method.

As an alternative thereto, the step d') can be based on machine learning. In this situation the detection can be regarded as a classification problem or as a regression problem. The vertebral bodies can be divided into three fracture grades, or no fracture is present. Alternatively, the severity of the fracture can be acquired as a numeric value. It is proposed to use a heterogeneous set of texture-specific features in order to determine the grade of the fracture. This can be combined with a rapid online selection of features in order to always use the most suitable set of features.

The proposed heterogeneous set of features contains inter alia 3D Haar-like features (object features which resemble Haar waveforms (rectangular functions) in their structure), HU (attenuation value of the X-ray radiation), Hu and Zernike image moments (Zernike moments are a sequence of polynomials which are orthogonal on the unit disk, Hu moments are particular invariant image moments), Antiga object features (whereby macularity, vessel similarity and plane surface are assessed), convergence index features of Kobatake and Hashimoto (stochastic method for assessing the convergence of data), and symmetry properties which describe the symmetry in the images.

One of the direct advantages of a learning-based approach is the fact that, in addition to the image properties, further characteristic values can be used for the training of the models. In particular, it is proposed to allow the inclusion of known risk factors for a vertebral fracture in the patient to be examined. Factors which influence a degeneration of the vertebral bodies are inter alia age, weight, delayed onset of the first period, known low bone density, known vertebral and non-vertebral fractures, smoking or the use of a walking aid.

A particularly advantageous variant of the method according to an embodiment of the invention is characterized in that the detection is effected using an approach which comprises a combination of geometric features and machine learning. First tests have shown that a combination of heterogeneous models results in a significant improvement in the predictive capability.

In a last step, the results found are characterized in respect of malignancy and type. This can be effected either likewise by way of a learning algorithm or by way of a classification query.

In place of a generally valid classification it is proposed to refer back to past vertebral fractures and to combine these with the associated clinical courses of treatment. A so-called discriminative learning is proposed, using a learning mechanism similar to the intrinsic "random forest" algorithm (Tsymbal, Huber, Zhou, Tran.CBR 2010; 3(1):1-16, the entire contents of which are hereby incorporated herein by reference).

Such a variant of the method according to an embodiment of the invention would not only offer the advantage of a reliable prediction for the fracture classification but could also be further expanded, for example the user could see displayed yet further evidence or instructions relating to the decision about the fracture type.

Furthermore, a variant would be conceivable wherein decision-making aids are offered for therapies and treatment methods. It would also be conceivable to output a treatment recommendation from corresponding databases. Naturally, a malignant fracture requires a different treatment than a benign fracture. The method according to the invention is able to differentiate malignant from benign fractures and recommend corresponding steps and treatments. At this point the same texture-based decision algorithm can be used as in step d').

A further advantage of an embodiment of the invention is the increased sensitivity with regard to the early discovery of vertebral fractures. Together with the enhanced detection and classification of the different fracture types, this can result in a better choice of therapy. Last but not least, the fully automated method saves time and can be applied to any routine CT measurement which may have been performed on the patient for completely different reasons.

An embodiment of the invention relates to a computed tomography system which includes a central processing unit or a computer for the evaluation of image data, wherein the method according to an embodiment of the invention is implemented on the central processing unit or the computer of the computed tomography system. Such a computed tomography system proves to be very advantageous because it enables fracture analyses to be carried out fully automatically.

Ideally the method according to an embodiment of the invention is part of a computer program for use with a central processing unit or a computer for the evaluation of image data from a computed tomography system.

By preference, the computer program containing the method according to the invention is stored on a data medium.

Alternatively, the computer program can however also be stored in a network to which the computer in the computed tomography system has access.

Figure 1:
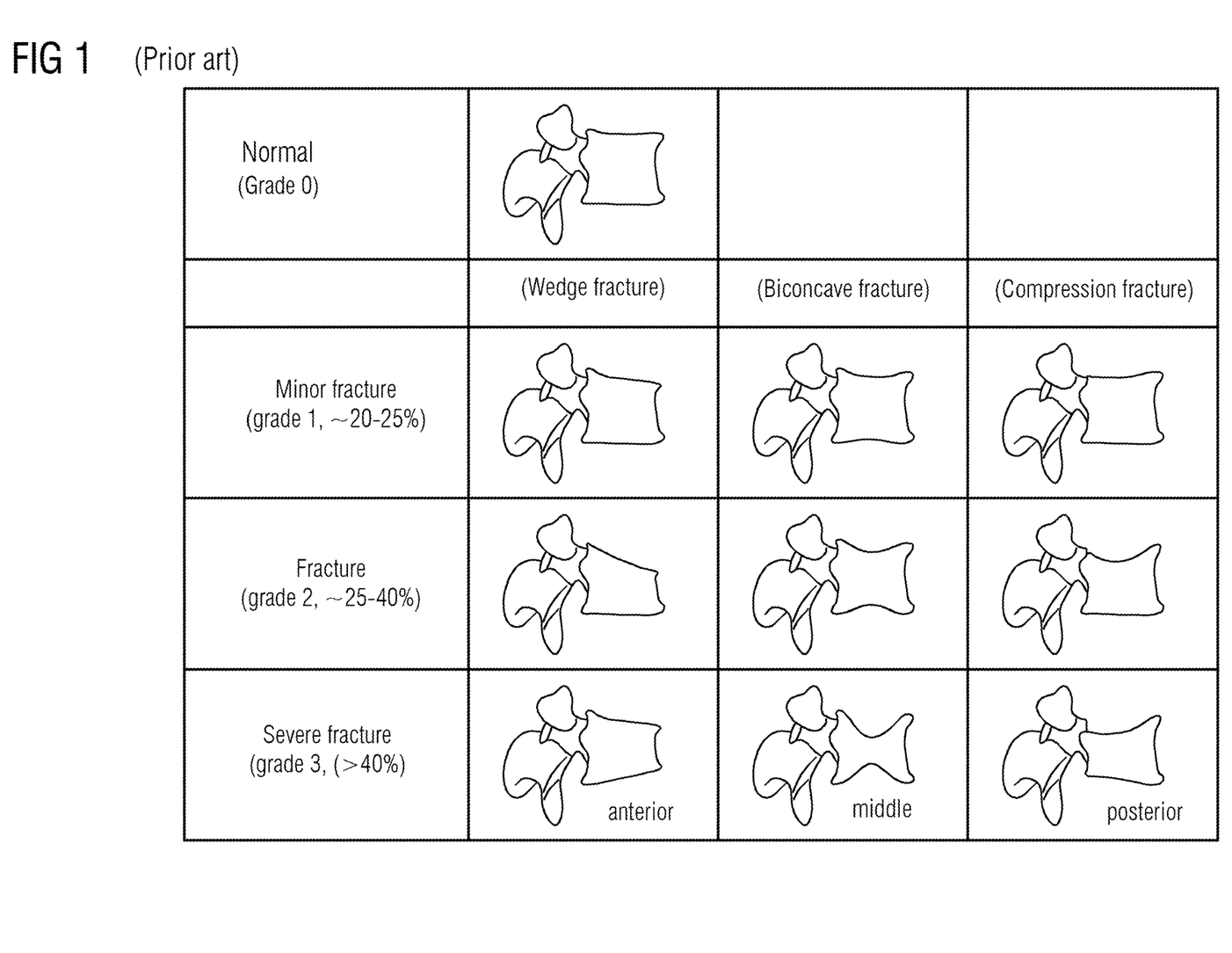
FIG. 1 shows a schematic illustration of the classification model according to Genant.

In order to determine the degree of vertebral body compression and the risk of a fracture, the height of the vertebral bodies is usually measured manually. Genant et al. have presented a semi-quantitative method by means of which the degree of degeneration of the vertebral bodies can be categorized from measuring the height of the vertebral bodies. The various categories of the Genant model are illustrated in FIG. 1.

Fractures are accompanied by a change in shape of the vertebral bodies, in particular the loss of parallelism of the endplates, breaks or cracks in the external bone structure (cortical bone) and usually a reduced anterior, middle or posterior height. The degree of the height loss determines the associated grade of the vertebral fracture. Fractures are categorized as wedge fracture, biconcave fracture or compression fracture, depending on whether the height loss is greatest in the anterior, middle or posterior region of the vertebral body. The degrees of severity of the fractures are dependent here on the relative loss in height.

For the determination of the bone density the CT scan of each vertebral body is divided into image slices. The algorithm commences with the middle slice and then works its way as far as the lower and upper endplates.

Figure 2:
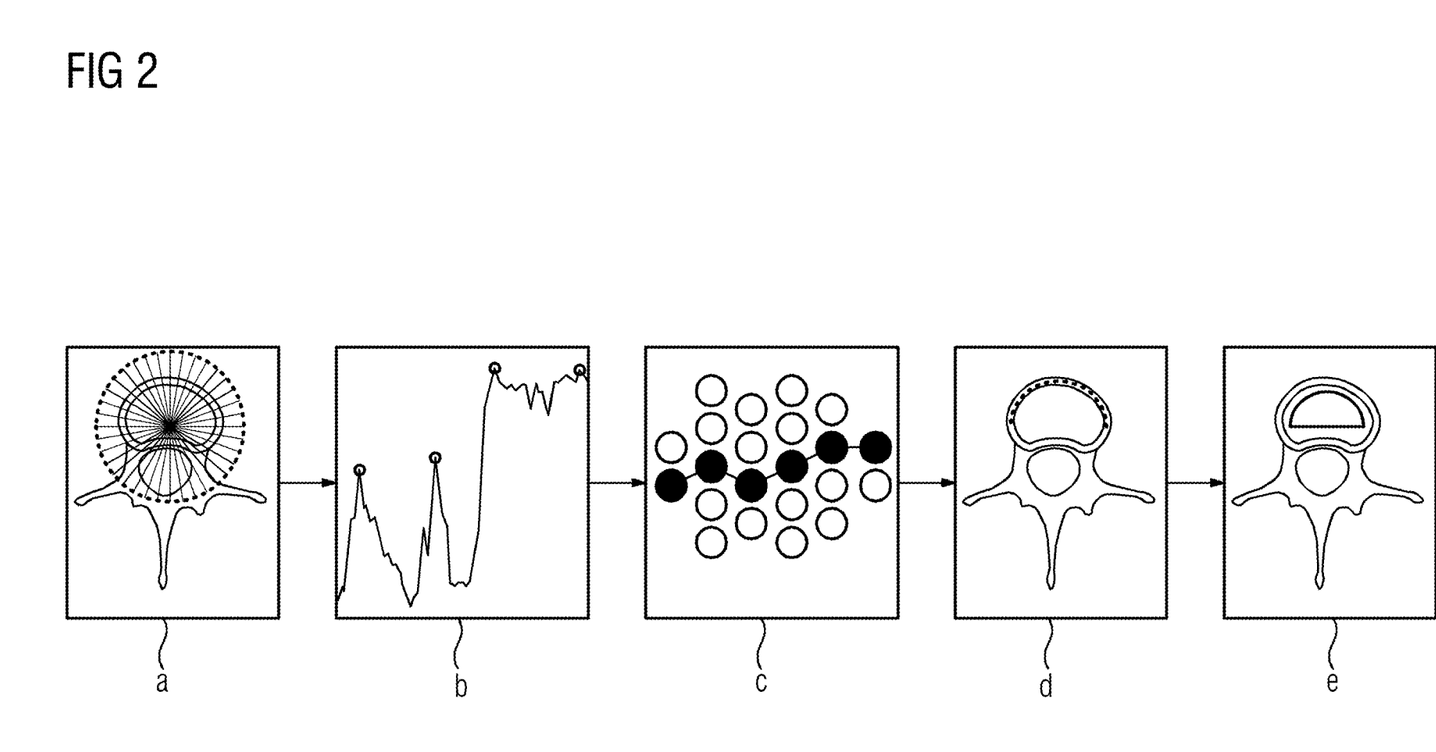
FIG. 2 shows a schematic illustration of the steps f) to i) of an exemplary embodiment of the method according to an embodiment of the invention.

A schematic illustration of the steps f) to i) is shown in FIG. 2. For each individual slice, virtual beam paths which run from the middle of the image slice to the edges are constructed (FIG. 2a).

The HU values along each beam produce a graph. The local maxima are determined with the aid of a low-pass filter (FIG. 2b). Only one of the maxima belongs to the contour of the cortical bone (corticalis).

In order to find this contour the maxima are used as nodes of a weighted (2D) graph. A "shortest path" algorithm is employed in order to find the optimum path between the maxima of all the beam paths (FIG. 2c).

In this situation, the algorithm decides on the basis of the HU value of the maxima and the path distance lying between the maxima which local maximum is used in each case for the determination of the contour of the vertebral body. (FIG. 2d)

When the contour has been determined, the contour is narrowed toward the middle (FIG. 2e).

Figure 3:
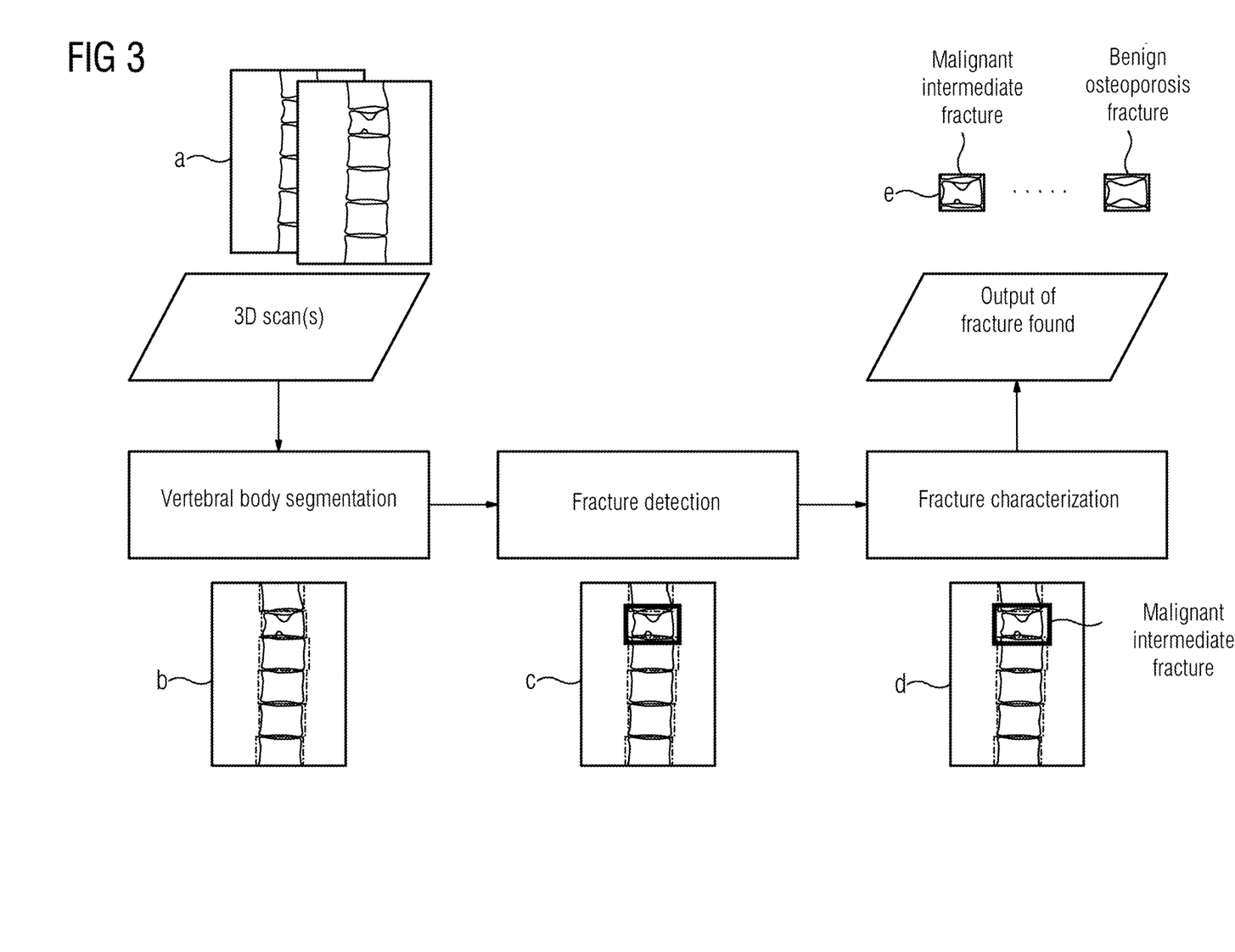
FIG. 3 shows a schematic illustration of the steps a) to f') of an exemplary embodiment of the method according to an embodiment of the invention.

FIG. 3 shows a schematic illustration of the steps a) to f) of an exemplary embodiment of the method according to the invention. The following method steps are illustrated:

Acquisition of at least one 3D CT scan of a person to be examined and detection of the spinal column in the CT image (FIG. 3a).

FIG. 3b shows the segmentation of the vertebral bodies in the CT image.

The detection of fractures is illustrated in FIG. 3c.

FIG. 3d shows the characterization of the fractures, in particular the division into benign and malignant.

The output of the results, divided into diagnostic categories, in particular malignancy and disease type, takes place in the last step, shown in FIG. 3e.

Figure 4:
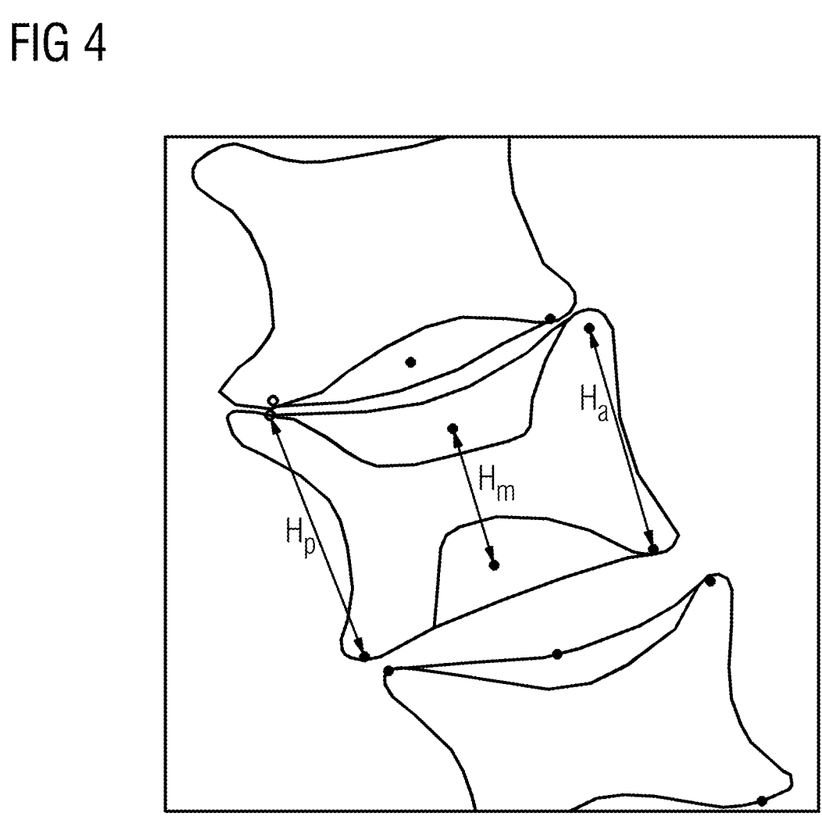
FIG. 4 shows a schematic illustration of the height determination of the vertebral body.

On the basis of a schematic illustration, FIG. 4 shows an example of the height determination of the vertebral body. The height of the vertebral body is determined at the front edge (anterior) $H_a$, in the middle $H_m$ and at the rear edge (posterior) $H_p$.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii)

object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:
   detecting at least one vertebral body in a computed tomography (CT) image, the CT image being based on at least one three-dimensional (3D) CT scan of a person to be examined;
   determining a contour of a cortical bone of the at least one vertebral body using an algorithm based upon measured Hounsfield Unit (HU) values;
   reducing the determined contour of the at least one vertebral body toward a center of the at least one vertebral body by a reducible marginal area or a reducible marginal volume to an inner area or an inner volume to exclude the cortical bone from a density measurement;
   determining density of the at least one vertebral body, wherein,
      in the determining of the contour, the contour of the cortical bone is ascertained based on the measured HU values along beam paths which run from a middle of the at least one vertebral body to an edge of the at least one vertebral body, and
      in the determining of the contour of the cortical bone, local maxima are ascertained based on the measured HU values along each beam path with an aid of a low-pass filter; and
   determining a probability of osteoporosis of the at least one vertebral body based on the determined density, wherein the algorithm comprises a shortest path algorithm.

2. The method of claim 1, further comprising:
   determining an average bone density value by determining average HU values for a region of interest in at least one of an inner and an outer area of the reducible marginal area or the reducible marginal volume or at least one of the inner and outer volume.

3. The method of claim 1, wherein normalized or calibrated CT attenuation values are ascertained on a basis of an accelerating voltage of an X-ray source used during provisioning of the CT image, and wherein average bone density value is ascertained from the normalized or calibrated CT attenuation values.

4. The method as claimed in claim 1, wherein the shortest path algorithm comprises a Dijkstra's algorithm.

5. The method of claim 2, further comprising:
   automatically comparing the determined average bone density value with reference data; and
   forming comparison statements from the automatic comparing, regarding a probability of an osteoporosis, as a function of the determined average bone density value.

6. The method as claimed in claim 5, wherein patient data is taken into consideration during the comparing with the reference data.

7. A computed tomography system, comprising:
   a central processor to evaluate image data, the central processor of the computed tomography system being configured to:
   detect at least one vertebral body in a computed tomography (CT) image, the CT image being based on at least one three-dimensional (3D) CT scan of a person to be examined;
   determine a contour of a cortical bone of the at least one vertebral body using an algorithm based upon measured Hounsfield Unit (HU) values with an aid of a low-pass filter;
   reduce the determined contour by a reducible marginal area or a reducible marginal volume to an inner area or an inner volume to exclude the cortical bone from a density measurement;
   determine density of the at least one vertebral body, wherein,
      in the determining of the contour, the contour of the cortical bone is ascertained based on the measured HU values along beam paths which run from a middle of the at least one vertebral body to an edge of the at least one vertebral body, and
      in the determining of the contour of the cortical bone, local maxima are ascertained based on the measured HU values along each beam path; and
   determine a probability of osteoporosis of the at least one vertebral body based on the determined density, wherein the algorithm comprises a shortest path algorithm.

8. A non-transitory computer readable medium comprising a computer program, for use with a central processor, to evaluate image data from a computed tomography system, the computer program including segments to implement the method of claim 1 when executed.

9. The method as claimed in claim 6, wherein the patient data includes age and known pre-existing conditions.

10. The computed tomography system of claim 7, wherein the central processor is further configured to determine an average bone density value using HU values in at least one of the inner and outer area or at least one of the inner and outer volume.

11. The computed tomography system of claim 10, wherein normalized or calibrated CT attenuation values are ascertained on a basis of an accelerating voltage of an X-ray source used during provisioning of the CT image, and wherein the average bone density value is ascertained from the normalized or calibrated CT attenuation values.

* * * * *